United States Patent [19]

Osdene et al.

[11] Patent Number: 5,138,062

[45] Date of Patent: Aug. 11, 1992

[54] NICOTINE ANALOGS

[75] Inventors: Thomas S. Osdene, Richmond; Henry V. Secor, Midlothian; Jeffrey I. Seeman, Richmond, all of Va.

[73] Assignees: Philip Morris Incorporated; Philip Morris Products Inc., New York

[21] Appl. No.: 618,913

[22] Filed: Nov. 28, 1990

Related U.S. Application Data

[62] Division of Ser. No. 416,523, Oct. 3, 1989, Pat. No. 5,015,741.

[51] Int. Cl.[5] .......................................... C07D 417/14
[52] U.S. Cl. .................................. 546/329; 546/330; 546/332
[58] Field of Search ................. 546/329, 330 CN, 332

[56] References Cited

FOREIGN PATENT DOCUMENTS 1195977 10/1985 Canada .
94766 11/1983 European Pat. Off. .

OTHER PUBLICATIONS

CA 100: 121105 (1983) (Abstract of EP above).

Primary Examiner—C. Warren Ivy
Assistant Examiner—Catherine Scalzo
Attorney, Agent, or Firm—James E. Schardt; George A. Depaoli

[57] ABSTRACT

This invention provides a class of nicotine analogs which as therapeutic agents exhibit tranquilizing effects in mammals.

Illustrative of an invention nicotine analog is 3-[N-methyl-N-(3-aminopropyl)]aminomethylpyridine

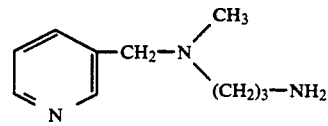

the nicotine analogs can exist in the form of acid addition salts.

4 Claims, No Drawings

NICOTINE ANALOGS

This application is a division of application Ser. No. 07/416,523, filed Oct. 3, 1989 now U.S. Pat. No. 5,015,741.

BACKGROUND OF THE INVENTION

Nicotine has been utilized as an insecticide for many years. Yamamoto has studied a number of nicotinoids (both natural and synthetic) with regard to their insecticidal activity [*Agr. Biol. Chem.*, 26, 709(1962); Id., 27, 445(1963); Id., 27, 450(1963); Id., 27, 684(1963); Id., 32, 568(1968); Id., 32, 747(1968); Id., 32, 1341(1968)]. Several of the analogs studied possess significant toxicity towards aphids, house flies, and cockroaches. U.S. Pat. Nos. 4,155,909; 4,321,387; and 4,332,945 describe the production of novel nicotine derivatives and the nature of their insecticidal activity.

Of the many nicotine analogs reported in the literature, the only ones having amino substituents on an intact nicotine ring skeleton are pyridine substituted derivatives, e.g., 2-amino- and 4-aminonicotine and 2-amino- and 4-aminocotinine [*Heterocycles*, 23, 1681(1985); *Chem. Ber.*,57, 1163(1924)].

U.S. Pat. No. 2,890,222 describes the production of quaternized nicotine salts such as 1-amino-1-methyl-2-(3-pyridyl)pyrrolidinium chloride. These quaternary salts have utility as insecticides, parasiticides and fungicides, and they are less toxic than nicotine to warm-blooded animals.

Other nicotine types of polyheterocyclic compounds have been found to exhibit beneficial pharmacodynamic activity in mammals. U.S. Pat. No. 3,991,197 describes pyrrolidinylpyridine compounds such as (2,2-dimethyl-5-phenyl-3-pyrrolidinyl)pyridine. Such compounds are characterized by analgesic activity.

U.S. Pat. No. 4,267,185 describes pyrrolylpiperidines such as 1,2,3,6-tetrahydro-1-methyl-4-(1-methylpyrrol-2-yl)pyridine, which are useful as antidepressant agents.

There is continuing interest in the development of pharmaceutical compositions such as psychotherapeutic agents, which are effective in low dosages without an unacceptable level of side effects. One productive approach to the development of biologically active molecules derives from the combination of structural classes or substructures from two or more types of compounds.

Accordingly, it is an object of this invention to provide a novel class of nicotine analogs and related structures.

It is another object of this invention to provide compounds which derive from the combination of tobacco alkaloid-type structures such as 2-(3-pyridyl)pyrrolidinyl-with a substituent such as 1,ω-diaminoalkyl.

It is a further object of this invention to provide nicotine derivatives which exhibit tranquilizing and muscle relaxing activities in mammals, without inducing nicotine-like effects such as hypertension and tachycardia.

Other objects and advantages of the present invention shall become apparent from the accompanying description and examples.

DESCRIPTION OF THE INVENTION

One or more objects of the present invention are accomplished by the provision of a nicotine derivative corresponding to the formula:

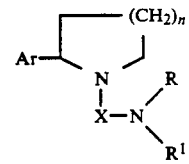

where R and $R^1$ are substituents selected from hydrogen and $C_1$–$C_4$ alkyl groups; R and $R^1$ when taken together with the connecting elements form an alicyclic structure; X is a divalent acyclic $C_2$–$C_{10}$ hydrocarbyl radical; Ar is an aromatic substituent having 4–12 carbon atoms; and n is an integer with a value of 1–3.

In another embodiment this invention provides an aromatic derivative corresponding to the formula:

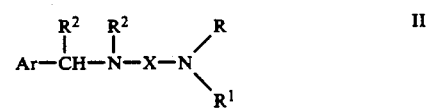

where R, $R^1$ and $R^2$ are substituents selected from hydrogen and $C_1$–$C_4$ alkyl groups; R and $R^1$ when taken together with the connecting elements form an alicyclic structure; X is a divalent acyclic $C_2$–$C_{10}$ hydrocarbyl radical; and Ar is an aromatic substituent having 4–12 carbon atoms.

In another embodiment this invention provides a nicotine analog corresponding the formula:

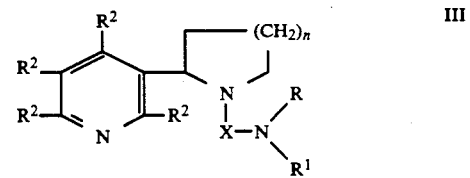

where R, $R^1$ and $R^2$ are substituents selected from hydrogen and $C_1$–$C_4$ alkyl groups; R and $R^1$ when taken together with the connecting elements form an alicyclic structure; X is a divalent acyclic $C_2$–$C_{10}$ hydrocarbyl radical; and n is an integer with a value of 1–3.

In a further embodiment this invention provides a nicotine analog corresponding to the formula:

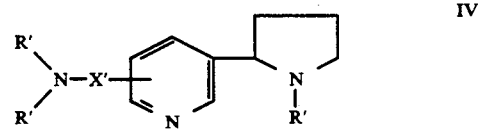

where R' is a $C_1$–$C_4$ alkyl group; and X' is a divalent acyclic $C_2$–$C_{10}$ hydrocarbyl radical.

In the formulae I–IV as represented above, R, $R^1$, $R^2$ and R' can be the same or different substituents. Illustrative of these substituents are hydrogen; alkyl groups containing between about 1–4 carbon atoms such as methyl, ethyl, propyl, isopropyl, butyl and isobutyl; and R and $R^1$ when taken together with the connecting elements can be an alicyclic group such as pyrrolyl, pyrrolidinyl, pyrazolinyl, piperidinyl, piperazinyl, morpholinyl, and the like.

In formulae I–II, the Ar substituent is illustrated by aromatic structures such as phenyl; tolyl; xylyl; 4-ethylphenyl; 4-methoxyphenyl; naphthyl; pyridyl; pyrazyl; pyridizyl; and the like.

Illustrative of X and X' in formulae I–IV are divalent acyclic $C_2$–$C_{10}$ hydrocarbyl radicals such as —$(CHR^3)_m$—, where m is an integer of 1–10, and $R^3$ is hydrogen or a $C_1$–$C_4$ alkyl group; alkylene; and the like.

The present invention nicotine analogs in general are derived from (R,S)-nornicotine as the basic structural starting material. Illustrative of a typical synthesis is the preparation of (R,S)-1-(3-aminopropyl)-2-(3-pyridyl)-pyrrolidine by the following reaction scheme:

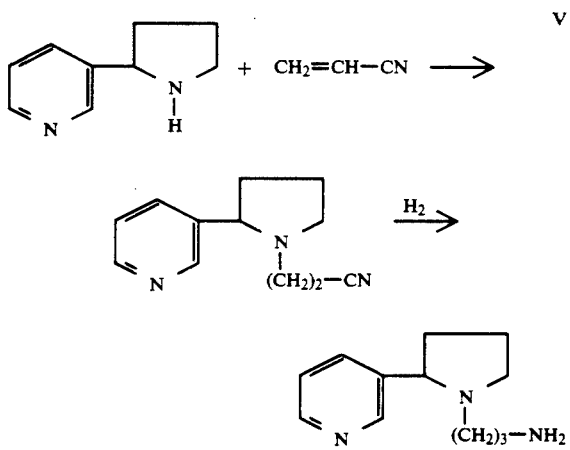

Some of the invention nicotine analogues in general are derived from 1-alkyl-1-arylmethylamines as the basic structural starting material. Illustrative of a typical synthesis is the preparation of 3-[N-methyl-N-[3-(N,N-dimethylamino)propyl]aminomethyl]pyridine by the following reaction scheme:

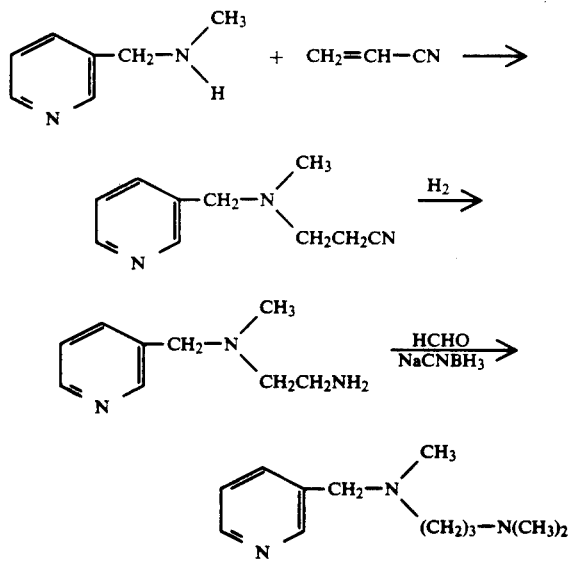

For molecules containing a piperidinyl- or azacyclohepta-ring system, analogs of anabasine or 2-(3-pyridyl)-1-azacycloheptane could be used as appropriate starting materials. As described below for nicotine analogs, either the racemic mixtures or particular enantiomers of specific compounds can be obtained and the methods for optical resolution or asymmetric synthesis can be similarly executed.

The nicotine analog product V illustrated above is a racemic mixture of (R,S)-enantiomers with respect to the 2'-position of the pyrrolidine structure:

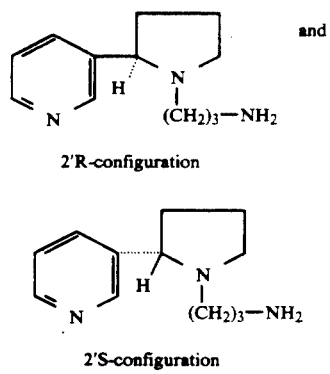

An optically pure nicotine analog can be obtained by employing either R or S nornicotine as the starting material, and obtaining a product which has either a R or S configuration at the 2'-position of the pyrrolidine ring.

Another method of obtaining optically pure nicotine analog antipodes is by the resolution of a (R,S) 2'-position racemic mixture. One method of resolution is by fractional crystallization of the racemic mixture which is in the form of a salt with an optically active carboxylic acid compound such as dibenzoyltartaric acid, camphorsulfonic acid, and the like.

The invention nicotine analog compounds contain at least two basic nitrogen atoms, and therefore can form acid addition salts with organic and inorganic acids such as hydrochloric acid, hydrobromic acid, sulfuric acid, acetic acid, succinic acid, maleic acid, ethanesulfonic acid, p-toluenesulfonic acid, and the like. The acid addition salts of the nicotine analogs also can be in the form of hydrates.

The present invention nicotine analogs exhibit pharmacological properties which are indicated for utility as potential psychotherapeutic agents.

The present invention nicotine analogs exhibit tranquilizing and muscle relaxing properties when administered to mammals. The nicotine analogs do not exhibit nicotine-like properties such as tachycardia, hypertension, gastrointestinal effects, emesis in dogs, and the like.

A present invention nicotine analog composition can be formulated into pharmaceutical preparations which contain a pharmaceutically acceptable organic or inorganic inert carrier material suitable for enteral or parenteral application, such as water, gelatin, lactose, starch, magnesium stearate, talc, vegetable oils, gum, polyalkylene glycols, Vaseline, and the like. The pharmaceutical preparations can be in solid form, e.g., as tablets, dragees, suppositories and capsules, or in liquid form, e.g., solutions, suspensions and emulsions. Such preparations can be sterilized and can contain pharmaceutically acceptable adjuvants such as preservatives, stabilizers, wetting agents, emulsifiers, salts for varying the osmotic pressure, or buffers. The preparations can also contain other therapeutically valuable substances.

A nicotine analog as a therapeutic agent can be employed in the form of a free base, but preferably is in the form of a pharmaceutically acceptable acid addition salt or salt hydrate. Salts can be formed with a pharmaceutically acceptable acid such as hydrochloric acid, sulfuric acid, phosphoric acid, nitric acid, hydrobromic acid, oxalic acid, maleic acid, succinic acid, benzoic acid, lactic acid, and the like.

A present invention nicotine analog can be administered to a mammal by any conventional means available for use in conjunction with pharmaceuticals, either as an individual therapeutic agent or in a combination of therapeutic agents. Administration can be parenterally, i.e., subcutaneously, intravenously, intramuscularly or intraperitoneally. Alternatively or concurrently, administration can be by the oral route.

The following examples are further illustrative of the present invention. The components and specific ingredients are presented as being typical, and various modifications can be derived in view of the foregoing disclosure within the scope of the invention.

EXAMPLE I (R,S)-1-(2-Cyanoethyl)-2-(3-pyridyl)pyrrolidine

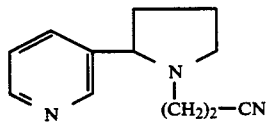

A solution of 15.0 g (0.101 mole) of (R,S)-nornicotine in 34 ml of water containing 0.27 g of sodium hydroxide is treated with 7.0 g (0.132 mole) of acrylonitrile over a 5 minute period while keeping the temperature less than 25° C. The solution is stirred for an additional 5 minutes, treated with 5 ml of 50% KOH and extracted with ether. The ethereal extract is dried ($Na_2SO_4$), concentrated and distilled bulb to bulb. A small amount of forerun [oven temperature up to 110° C. (0.025 torr)] is discarded and 19.13 g (93.8%) of product is collected as a clear colorless oil: bp [oven temperature 110°–130° C. (0.025 torr)].

$^1$H NMR ($CDCl_3$) δ1.55–2.28 (m, 4H), 2.30–3.00 (m, 7H), 3.33–3.56 (m, 2H), 7.33 (ddd, 1H, J=1.0, 5.0, 8.0 Hz), 7.83 (dt, 1H, J=2.0, 8.0 Hz), 8.52 (m, 2H).

Anal. Calc. for $C_{12}H_{15}N_3$: C, 71.61; H, 7.51; N, 20.88. Found: C, 71.36; H, 7.49; N, 20.96.

EXAMPLE II (R,S)-1-(3-Aminopropyl)-2-(3-pyridyl)pyrrolidine

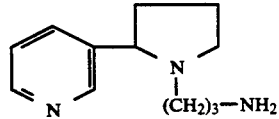

A solution of 10.5 g of (R,S)-1-(2-cyanoethyl)-2-(3-pyridyl)pyrrolidine in 200 ml of ammonia saturated ethanol and 5.0 g of activated Raney nickel is hydrogenated in a Parr apparatus for 12 hours at 47 psi. The catalyst is removed by filtration. The filtrate is concentrated and the resulting oily residue is taken up in methanol and dried ($Na_2SO_4$). The solution is concentrated and distilled bulb to bulb [oven temperature 125° C. (0.025 torr)] to yield 9.4 g (87.7%) of product as a clear colorless oil: picrate, mp 239°–240° C.

$^1$H NMR ($CDCl_3$) δ1.25 (s, 2H), 1.38–2.78 (m, 11H), 3.15–3.50 (m, 2H), 7.25 (ddd, 1H, J=1.0, 5.0, 8.0 Hz), 7.70 (dt, 1H, J=3.0, 8.0 Hz), 8.50 (dd, 1H, J=2.0, 5.0 Hz), 8.55 (br d, 1H, J=2.0 Hz).

Anal. (tripicrate) Calc. for $C_{30}H_{28}N_{12}O_{21}$: C, 40.35; H, 3.14; N, 18.83. Found: C, 40.56; H, 3.46; N, 18.79.

EXAMPLE III (R,S)-1-(3-Dimethylaminopropyl)-2-(3-pyridyl)pyrrolidine

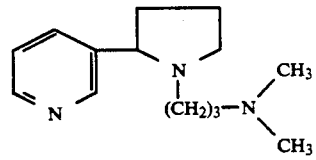

A solution of 2.0 g (9.74 mmole) of (R,S)-1-(3-aminopropyl)-2-(3-pyridyl)pyrrolidine in 25 ml of acetonitrile is treated with 3.5 ml of 37% aqueous formaldehyde, cooled to 0° C. and treated with 0.8 g (12.7 mmole) of sodium cyanoborohydride. The solution is stirred at 0°–5° C. for 30 minutes, treated with a trace of bromocresol green indicator followed by 2N HCl in acetonitrile (16.4 ml of conc. HCl diluted to 100 ml with acetonitrile) to give a yellow color. The addition of 2N HCl in acetonitrile is continued for 2 hours to maintain a yellow color, and the solution is then stirred for several hours.

The solution is concentrated on a rotary evaporator and the resulting residue is dissolved in water and the aqueous phase is washed with ether. The aqueous phase is then treated with base (50% KOH) and extracted with ether. This crude material shows evidence of mono-methylated product, and is further treated with 2 ml of formic acid and 1 ml of 37% aqueous formaldehyde, heated under reflux for 3 hours, acidified (HCl), and washed with ether. The aqueous phase is basified (50% KOH), extracted with ether and concentrated.

Final purification is accomplished employing a Harrison Chromatotron ®. The major band is collected as one fraction from a 4 mm plate using a chloroform, ethanol and ammonium hydroxide (85-14-1) solvent system.

The solvent is removed on a rotary evaporator and the residue distilled bulb to bulb at an oven temperature of 120°–125° C. (0.025 torr) to give 1.36 g (59.9%) of product as a clear odorless oil.

$^1$H NMR ($CDCl_3$) δ1.45–2.64 (m, 11H), 2.16 (s, 6H), 3.15–3.49 (m, 2H), 7.23 (ddd, 1H, J=0.8, 5.0, 8.0 Hz), 7.68 (dt, 1H, J=2.0, 5.0 Hz), 8.46 (dd, 1H, J=2.0, 5.0 Hz), 8.53 (br d, 1H, J=2.0 Hz).

Anal. Calc. for $C_{14}H_{23}N_3$: C, 72.05; H, 9.94; N, 18.01. Found: C, 72.22; H, 10.18; N, 18.17.

EXAMPLE IV (R,S)-1-(2-Aminoethyl)-2-(3-pyridyl)pyrrolidine

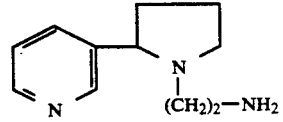

Employing the procedure of Example II, and (R,S)-N'-cyanomethylnornicotine as the starting material [J. Med. Chem., 19, 1168 (1976)], 12.0 g (83.4%) of product is obtained as a clear colorless oil: bp 115° C. (oven)/0.025 torr.

$^1$H NMR (CDCl$_3$) δ1.23 (s, 2H), 1.53–2.85 (m, 9H), 3.23–3.50 (m, 2H), 7.25 (ddd, 1H, J=0.8, 5.0, 8.0 Hz), 7.73 (dt, 1H, J=2.0, 8.0 Hz), 8.50 (dd, 1H, J=2.0, 5.0 Hz), 8.56 (br d, 1H, J=2.0 Hz).

Anal. Calc. for C$_{11}$H$_{17}$N$_3$: C, 69.07; H, 8.96; N, 21.97. Found: C, 68.97; H, 8.89; N, 22.09.

EXAMPLE V (R,S)-1-(2-Dimethylaminoethyl)-2-(3-pyridyl)pyrrolidine

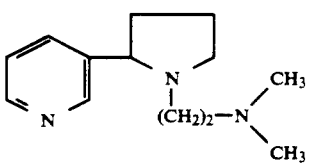

In accordance with the procedure of Example III, 2.8 g of (R,S)-1-(2-aminoethyl)-2-(3-pyridyl)pyrrolidine is methylated to give 1.50 g (46.8%) of the desired product as a clear colorless oil: bp 105° C. (oven)/0.025 torr.

$^1$H NMR (CDCl$_3$) δ1.60–2.85 (m, 9H), 2.15 (s, 6H), 7.30 (dd, 1H, J=5.0, 8.0 Hz), 7.75 (dt, 1H, J=2.0, 8.0 Hz), 8.50 (dd, 1H, J=2.0, 5.0 Hz), 8.58 (br d, 1H, J=2.0 Hz).

Anal. Calc. for C$_{13}$H$_{21}$N$_3$: C, 71.19; H, 9.65; N, 19.16. Found: C, 70.91; H, 9.69; N, 19.48.

EXAMPLE VI (R,S)-1-(3-Cyanopropyl)-2-(3-pyridyl)pyrrolidine

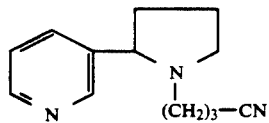

A solution of 5.0 g (33.8 mmole) of (R,S)-nornicotine and 6.41 g (42.25 mmole) of 1,8-diazabicyclo[5.4.0]undec-7-ene (DBU) in 50 ml of acetonitrile is cooled to 0° C., and treated with 6.26 g (42.25 mmole) of 4-bromobutyronitrile. The solution is stirred at 0° C., and treated with 6.26 g (42.25 mmole) of 4-bromobutyronitrile. The solution is stirred at 0° C. for 2 hours and at room temperature for 72 hours. The solution is acidified with 6N HCl, and washed with ether. The aqueous phase is basified (50% KOH), extracted with ether, and the ether extract is dried (Na$_2$SO$_4$) and concentrated. The residual oil is distilled bulb to bulb, and the fraction distilling at an oven temperature of 135°–150° C. (0.025 torr) is 3,83 g (52.6%) of product as a light yellow oil.

$^1$H NMR (CD$_2$Cl$_2$) δ1.44–2.0 (m, 5H), 2.0–2.63 (m, 6H), 3.10–3.35 (m, 2H), 7.20 (ddd, 1H, J=0.8, 5.0, 8.0 Hz), 7.63 (dt, 1H, J=2.0, 5.0 Hz), 8.33–8.23 (m, 2H).

Anal. Calc. for C$_{13}$H$_{17}$N$_3$: C, 72.52; H, 7.96; N, 19.52. Found: C, 72.24; H, 7.88; N, 19.30.

EXAMPLE VII (R,S)-1-(4-Aminobutyl)-2-(3-pyridyl)pyrrolidine

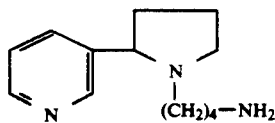

In accordance with the procedure of Example II, 2.0 g of (R,S)-1-(3-cyanopropyl)-2-(3-pyridyl)pyrrolidine is hydrogenated to yield 1.4 g of product as a clear colorless oil: bp 130° C. (oven)/0.02 torr.

$^1$H NMR (CD$_2$Cl$_2$) δ1.15–1.40 (m, 5H), 1.45–2.28 (m, 8H), 2.45 (br t, 2H, J=9.6 Hz), 3.04–3.35 (m, 2H), 7.14 (ddd, 1H, J=0.8, 5.0, 8.0 Hz), 7.60 (dt, 1H, J=2.0, 8.0 Hz), 8.33 (dd, 1H, J=2.0, 5.0 Hz), 8.42 (br d, 1H, J=2.0 Hz).

Anal. Calc. for C$_{13}$H$_{21}$N$_3$: C, 71.19; H, 9.65; N, 19.16. Found: C, 71.18; H, 9.63; N, 18.91.

When (R,S)-1-(4-cyanobutyl)-2-(3-pyridyl)pyrrolidine is the starting material, the product obtained is (R,S)-1-(5-aminopentyl)-2-(3-pyridyl)pyrrolidine.

EXAMPLE VIII (R,S)-1-(4-Dimethylaminobutyl)-2-(3-pyridyl)pyrrolidine

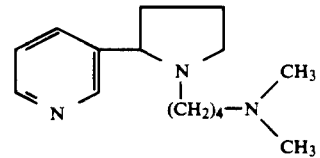

In accordance with the procedure of Example III, 1.3 g of (R,S)-1-(4-aminobutyl)-2-(3-pyridyl)pyrrolidine is methylated to 1.07 g (73%) of product as a clear colorless oil: bp 125° C. (oven)/0.03 torr.

$^1$H NMR (CDCl$_3$) δ1.10–1.43 (m, 4H), 1.44–2.53 (m, 8H), 1.99 (s, 6H), 7.13 (ddd, 1H, J=0.8, 2.0, 8.0 Hz), 7.36 (dt, 1H, J=2.0, 8.0 Hz), 8.34 (dd, 1H, J=2.0, 5.0 Hz), 8.41 (br d, 1H, J=2.0 Hz).

Anal. Calc. for C$_{15}$H$_{25}$N$_3$: theor. mass, 247.2048; M+ meas. mass, 247.2014

EXAMPLE IX (R,S)-1-(1-Piperidinyl)-3-[1-(2-pyridyl)pyrrolidinyl]-propane

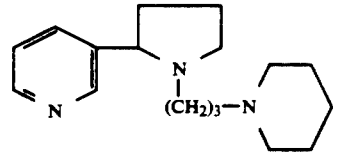

A solution of 2.0 g (10.14 mmoles) of (R,S)-1-(3-aminopropyl)-2-(3-pyridyl)pyrrolidine from Example II in 50 ml of ether is cooled to −70° C. under an atmosphere of nitrogen and treated with 7.10 ml (11.15 mmole) of 1.57M n-butyllithium in hexane over a 5 minute period. The resulting suspension of a yellow precipitate is stirred for 15 minutes at −70° C. and then treated with 2.44 g (10.64 mmole) of 1,5-dibromopentane. The solution is stirred for 1 hour at −70° C. and for 18 hours at room temperature then treated with basic (50% KOH) and extracted with ether. The ether solution is concentrated and the resulting yellow colored residue is distilled bulb to bulb at an oven temperature of 150° C. (0.025 torr) to yield 1.87 g of a clear colorless oil.

Purification is accomplished with a Harrison Chromatotron ®. The major band is collected as one fraction from a 4 mm plate using a petroleum ether, acetone and triethylamine (80-50-8) solvent system. Bulb to bulb distillation of the concentrated fraction at an oven temperature of 135° C. (0.005 torr) yields 580 mg (21.8%) of product as a clear colorless oil.

$^1$H NMR (CDCl$_3$) δ1.35-2.70 (m, 21H), 3.13-3.53 (m, 2H), 7.23 (ddd, 1H, J=0.8, 4.8, 7.8 Hz), 7.67 (dt, 1H, J=7.8, 2.0 Hz), 8.49 (dd, 1H, J=4.8, 2.0 Hz), 8.53 (br d, 1H, J=2.0 Hz).

Anal. Calc. for C$_{17}$H$_{27}$N$_3$: theor. mass, 273.2205; M+ meas. mass, 273.2205.

EXAMPLE X (R,S)-2-(3-Pyridyl)pyrrolidin-1-yl)-3-pyrrolidin-1-yl)propane

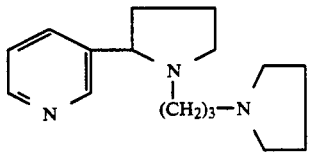

In accordance with the procedure of Example IX, 2.0 g of (R,S)-1-(3-aminopropyl)-2-(3-pyridyl)-pyrrolidine from Example II and 2.3 g (10.6 mmole) of 1,4-dibromobutane are reacted to form 500 g (19%) of product as a clear colorless oil: bp 140° C. (oven)/0.005 torr.

$^1$H NMR (CD$_2$Cl$_2$) δ1.27-2.65 (m, 19H), 3.08-3.35 (m, 2H), 7.13 (ddd, 1H, J=0.8, 4.8, 7.8 Hz), 7.61 (dt, 1H, J=2.1, 7.8 Hz), 8.35 (dd, 1H, J=4.8, 2.1 Hz), 8.42 (br d, 1H, J=2.1 Hz).

Anal. Calc. for C$_{16}$H$_{25}$N$_3$: theor. mass, 259.2048; M+ mass, 259.2013

EXAMPLE XI (R,S)-2-(3-Pyridyl)-1-[2-(4-morpholinyl)ethyl]pyrrolidine

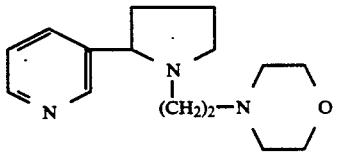

A solution of 2.39 g (16.1 mmole) of (R,S)-nornicotine in 75 ml of ether is stirred and cooled under nitrogen to −78° C. and slowly treated with 12.3 ml (17.7 mmoles) of 1.44M n-butyllithium in hexane. The resulting mixture is treated with a solution of 2.55 g (17.1 mmole) of N-chloroethylmorpholine in 10 ml of ether and is stirred at room temperature for 18 hours. The reaction mixture is basified (50% KOH), extracted with ether and concentrated. The resulting residual oil is distilled bulb-to-bulb at an oven temperature of 90°-130° C. (0.05 torr) to give 2.13 g of a pale yellow oil. Purification is carried out using a Harrison Chromatotron ®. The major band is collected from a 4 mm plate using a chloroform, ethanol and ammonium hydroxide (85-14-1) solvent system. The solvent is removed and the residue distilled bulb-to-bulb at an oven temperature of 130° C. (0.02 torr) to yield 1.91 g (45.3%) of product as a pale yellow oil.

$^1$H NMR (CDCl$_3$) δ1.55-2.58 (m, 12H), 2.62-2.98 (m, 1H), 3.23-3.53 (m, 2H), 3.55-3.79 (m, 4H), 7.27 (ddd, 1H, J=0.8, 5.0, 8.0 Hz), 7.78 (dt, 1H, J=2.0, 8.0 Hz), 8.54 (dd, 1H, J=2.0, 5.0 Hz), 8.58 (br d, 1H, J=2.0 Hz).

Anal. Calc. for C$_{15}$H$_{23}$N$_3$O: C, 68.93; H, 8.87; N, 16.08. Found: C, 68.73; H, 9.00; N, 16.21.

EXAMPLE XII 4-(3-Bromopropionyl)-1-piperazinecarboxaldehyde

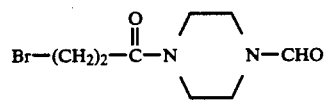

A mixture of 15 ml of water and 25 ml of methylene chloride containing 3.0 g (36 mmole) of sodium bicarbonate and 2.82 g (24.7 mmole) of 1-piperazinecarboxaldehyde is stirred and treated with 5.0 g (30.9 mmole) of 3-bromopropionyl chloride in 10 ml of methylene chloride over a 15 minute period while maintaining a temperature of about 20° C. After stirring for an additional 20 minutes, the organic phase is separated and the aqueous phase is extracted with methylene chloride. The combined organic phases are dried (Na$_2$SO$_4$), filtered and concentrated under high vacuum to yield 4.35 g (70.2%) of product as a colorless solid: mp 96°-98° C.

$^1$H NMR (CDCl$_3$) δ2.88 (t, 2H, J=8.2 Hz), 3.25-3.62 (m, 8H), 3.63 (t, 2H, J=8.2 Hz), 8.06 (s, 1H).

Anal. Calc. for C$_8$H$_{13}$BrN$_2$O$_2$: C, 38.57; H, 5.26; N, 11.24. Found: C, 38.69; H, 5.36; N, 11.19.

EXAMPLE XIII (R,S)-4-Formyl-1-[3-[2-(3-pyridyl)pyrrolidin-1-yl]propionyl]piperazine

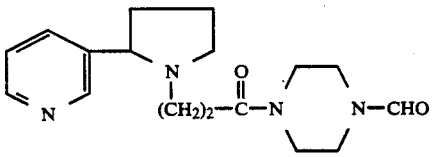

A solution of 2.21 g (15 mmole) of (R,S)-nornicotine in 40 ml of acetonitrile is treated with 2.29 g (15 mmole) of 1,8-diazabicyclo[5.4.0]undec-7-ene and 3.75 g (15 mmole) of 4-(3-bromopropionyl)-1-piperazinecarboxaldehyde. After standing for 2 days at room temperature the solution is concentrated at reduced pressure and finally at high vacuum at 160° C. to remove volatile impurities to give 4.75 g of crude product. Purification is achieved by the procedure described in Example IX using the same solvent system. The solvent is removed under high vacuum to yield the product as a colorless viscous oil.

$^1$H NMR (CDCl$_3$) δ1.53-3.05 (m, 9H), 3.25-3.58 (m, 10H), 7.28 (dd, 1H, J=4.6, 8.0 Hz), 7.68 (dt, 1H, J=2.0, 8.0 Hz), 8.08 (s, 1H), 8.50 (dd, 1H, J=2.0, 4.6 Hz), 8.60 (br d, 1H, J=2.0 Hz).

EXAMPLE XIV (R,S)-2-(3-Pyridyl)-1-[3-(4-methyl-1-piperazinyl)-propyl]pyrrolidine

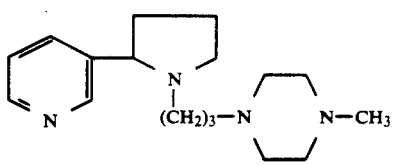

A solution of 1.2 g (3.8 mmole) of (R,S)-4-formyl-1-[3-[2-(3-pyridyl)pyrrolidin-1-yl]propionyl]piperazine in 30 ml of tetrahydrofuran is treated with 20 ml of (21.2 mmole) of 1.06M BH$_3$ in tetrahydrofuran, and then heated and stirred under reflux for 24 hours. The reaction mixture is cooled, treated with 26 ml of 6N hydrochloric acid, heated under reflux for 3 hours and concentrated under reduced pressure. The residue is dissolved in water, and the solution is filtered. The filtrate is washed with ether, basified (50% KOH), and extracted with ether. The dried (Na$_2$SO$_4$) ether extract is concentrated and distilled bulb-to-bulb at an oven temperature of 120° C. (0.005 torr) to yield 350 mg of product as a colorless viscous oil.

$^1$H NMR (CDCl$_3$) δ2.27 (s, 3H), 2.40 (s, 8H), 1.52–2.65 (m, 12H), 3.30 (br t, 1H, J=8.2 Hz), 7.25 (dd, 1H, J=4.8, 8.2 Hz) 7.73 (dt, 1H, J=2.0, 8.2 Hz), 8.50 (dt, 1H, J=2.0, 4.1 Hz), 8.55 (br d, 1H, J=2 Hz).

Anal. Calc. for C$_{17}$H$_{28}$N$_4$: C, 70.79; H, 9.79; N, 19.43. Found: C, 70.53; H, 9.93; N, 19.28.

EXAMPLE XV (R,S)-1-(2-cyanoethyl)-2-(6-methyl-3-pyridyl)pyrrolidine

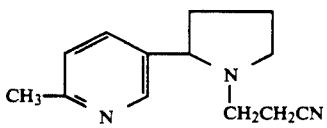

Employing the procedure in Example I, and (R,S)-6-methylnornicotine on the starting material, 11.4 g (85%) of the title product is obtained as a clear colorless oil after distillation at an oven temperature of 120° C. (0.07 torr).

$^1$H NMR (CD$_2$Cl$_2$) δ1.42–2.90 (m, 6H), 2.45 (s, 3H), 3.3 (br t, 2H, J=7.0 Hz), 7.11 (d, 1H, J=9.0 Hz), 7.64 (dd, 1H, J=9.0, 2.0 Hz), 8.36 (br d, 1H, J=2.0 Hz).

Anal. Calc. for C$_{13}$H$_{17}$N$_3$: C, 72.52; H, 7.96; N, 19.52. Found: C, 72.34; H, 8.12; N, 19.39.

EXAMPLE XVI (R,S)-1-(3-Aminopropyl)-2-(6-methyl-3-pyridyl)pyrrolidine

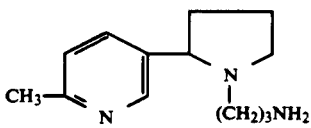

Employing the procedure of Example II, and (R,S)-1-(2-cyanoethyl)-2-(6-methyl-3-pyridyl)pyrrolidine as the starting material, 6.2 g (94%) of the title product is obtained as a clear colorless oil after the distillation at an oven temperature of 115° C. (0.08 torr).

$^1$H NMR (CDCl$_3$) δ1.32–2.70 (m, 9H), 2.07 (br s, 2H), 2.45 (s, 3H), 3.05–3.41 (m, 2H), 7.09 (d, 1H, J=8.0 Hz), 7.58 (dd, 1H, J=8.0, 2.2 Hz), 8.36 (br d, 1H, J=2.2 Hz).

Anal. (tripicrate, mp 208°-9° C.) Calc. for C$_{31}$H$_{30}$N$_{12}$O$_{21}$: C, 41.07; H, 3.34; N, 18.54. Found: C, 41.05; H, 3.35; N, 18.60.

EXAMPLE XVII (R,S)-1-[3-(N,N-Dimethylamino)propyl]-2-(6-methyl-3-pyridyl)pyrrolidine

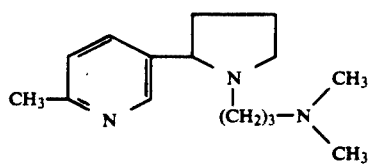

Employing the procedure of Example III, and (R,S)-1-(3-aminopropyl)-2-(6-methyl-3-pyridyl)pyrrolidine as the starting material, 1.7 g (75%) of the title product is obtained after distillation at an oven temperature of 110° C. (0.02 torr).

$^1$H NMR (CDCl$_3$) δ1.54–1.70 (m, 3H), 1.78–1.95 (m, 2H), 2.–2.35 (m, 5H), 2.17 (s, 6H), 2.44–2.52 (m, 1H), 2.54 (s, 3H), 3.23 (t, 1H, J=8.4 Hz), 3.35 (dd, 1H, J=6.5, 0.53 Hz), 7.11 (d, 1H, J=8.0 Hz), 7.57 (dd, 1H, J=8.0, 3.3 Hz), 8.4 (d, 1H, J=3.3 Hz); $^{13}$C NMR (CDCl$_3$) δ22.53, 24.06, 27.06, 35.15, 45.48, 52.48, 53.56, 57.81, 67.49, 123.05, 135.30, 136.32, 148.70, 156.94.

Anal. (tripicrate, mp 208° C.) Calc. for C$_{33}$H$_{34}$N$_{12}$O$_{21}$: C, 42.40; H, 3.67; N, 17.98. Found: C, 42.37; H, 3.44; N, 17.96.

EXAMPLE XVIII (1'R,2R,S)- and (1'S,2R,S)-1-(2-cyano-1-methylethyl)-2-(3-pyridyl)pyrrolidine

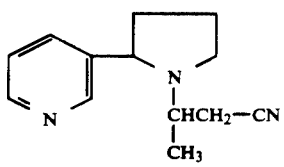

A mixture of 1.0 g (6.75 mmoles) of (R,S)-nornicotine, 2.0 ml of 2.4M sodium hydroxide and 2.27 g (34.4 mmoles) of crotonitrile is heated and stirred at 85° C. for 12 hours. The mixture is cooled, diluted with 10% acetic acid and extracted with ether. The ethereal phase is extracted with 5% HCl, and the acid extract is basified (50% KOH) and then extracted with ether. Evaporation of the ether followed by bulb-to-bulb distillation yields 1.15 g (79%) of the title product as a colorless oil by distillation at an oven temperature of 150° C. (0.01 torr).

NMR indicates that the product exists as a 1.6–1.0 mixture of diastereomers due to the presence of the chiral atom on the 2-cyano-1-methylethyl side chain.

$^1$H NMR (CDCl$_3$) δ (d, 38% of 3H, J=3.6 Hz), 1.18 (d, 62% of 3H, J=3.6 Hz).

Anal. (dipicrate, mp 154°–6° C.) Calc. for C$_{25}$H$_{23}$N$_9$O$_{14}$: C, 44.58; H, 3.44; N, 18.72. Found: C, 44.48; H, 3.67; N, 18.53.

EXAMPLE XIX (1′R,2R,S)- and (1′S,2RS)-1-(3-Amino-1-methylpropyl)-2-(3-pyridyl)-pyrrolidine

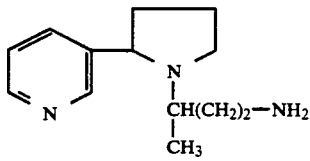

Employing the procedure of Example II, and (1′R,2RS)- and (1′S,2RS)-1-(2-cyano-1-methylethyl)-2-(3-pyridyl)pyrrolidine as the starting material, 506 mg (81%) of the title product is obtained as a colorless oil after distillation at an oven temperature of 135° C. (0.01 torr).

NMR indicates the product exists as a 8:5 mixture of diasteromers due to the presence of the chiral atom on the 3-amino-1-methylpropyl side chain.

$^1$H NMR (CDCl$_3$) δ0.91 (d, 38% of 3H, J=3.6 Hz), 1.02 (d, 62% of 3H, J=3.6 Hz).

Anal. (tripicrate, mp 207°–8° C.) Calc. for C$_{31}$H$_{30}$N$_{12}$O$_{21}$: C, 41.07; H, 3.34; N, 18.53. Found: C, 40.91; H, 3.30; N, 18.31.

EXAMPLE XX (R,S)-1-(2-Cyanoethyl)-2-phenylpyrrolidine

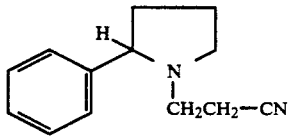

Employing the procedure of Example I, and 8.5 g of (R,S)-2-phenylpyrrolidine as the starting material, 9.73 g (83.9%) of the title product is obtained as a clear colorless oil after distillation at an oven temperature of 120° C. (0.01 torr).

$^1$H NMR (CDCl$_3$) δ1.58–3.02 (m, 9H), 3.25–3.50 (m, 2H), 7.23–7.48 (m, 5H).

Anal. Calc. for C$_{13}$H$_{16}$N$_2$: C, 77.96; H, 8.05; N, 3.99. Found: C, 77.91; H, 8.24; N, 14.21.

EXAMPLE XXI (R,S)-1-(3-Aminopropyl)-2-phenylpyrrolidine

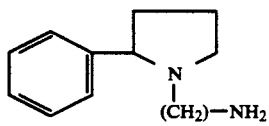

In accordance with the procedure of Example II, and (R,S)-1-(2-cyanoethyl)-2-phenylpyrrolidine as the starting material, 6.73 g (94.3%) of the title product is obtained as a clear colorless oil after distillation at an oven temperature of 130° C. (0.02 torr).

$^1$H NMR (CDCl$_3$) δ1.10 (br s, 2H), 1.3–2.30 (m, 8H), 2.52 (t, 1H, J=8.0 Hz), 2.68 (t, 2H, J=7.0 Hz), 3.10–3.48 (m, 2H), 7.20–7.43 (m, 5H).

Anal. Calc. for C$_{13}$H$_{20}$N$_2$: C, 76.42; H, 9.87; N, 13.71. Found: C, 76.19; H, 9.66; N, 13.83.

EXAMPLE XXII (R,S)-1-[3-(N,N-Dimethylamino)propyl]-2-phenylpyrrolidine

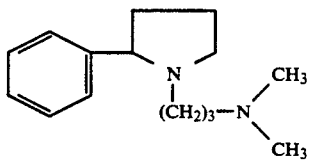

Employing the procedure of Example III, and (R,S)-1-(3-aminopropyl)-2-phenylpyrrolidine as the starting material, 5.2 g (69.9%) of the title product is obtained as a clear colorless oil after distillation at an oven temperature of 105° C. (0.01 torr).

$^1$H NMR (CDCl$_3$) δ1.45–2.73 (m, 11H), 2.18 (s, 6H), 3.08–3.50 (m, 2H), 7.22–7.43 (m, 5H).

Anal. (dipicrate, mp 176°–9° C.) Calc. for C$_{27}$H$_{30}$N$_8$O$_{14}$: C, 46.96; H, 4.38; N, 16.23. Found: C, 47.07; H, 4.56; N, 16.30.

EXAMPLE XXIII

3-[N-(2-Cyanoethyl)-N-methylaminomethyl]pyridine

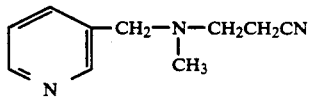

Employing the procedure of Example I, and N-methyl-3-pyridylmethylamine as the starting material [Acta. Chem. Scand., 17, 1717 (1963)] 12.2 g (84.9% of the title product is obtained as a clear colorless oil after distillation at an oven temperature of 135° C. (0.02 torr).

$^1$H NMR (CDCl$_3$) δ2.29 (s, 3H), 2.45–2.88 (m, 4H), 3.61 (s, 2H), 7.30 (dd, 1H, J=8.0, 5.2 Hz), 7.78 (dt, 1H, J=8.0, 2.0 Hz), 8.53–8.61 (m, 2H).

Anal. (dipicrate, mp 180°–1° C.) Calc. for C$_{22}$H$_{19}$N$_9$O$_{14}$: C, 41.71; H, 3.02; N, 19.15. Found: C, 41.76; H, 3.11; N, 19.24.

EXAMPLE XXIV

3-[N-Methyl-N-(3-aminopropyl)]aminomethylpyridine

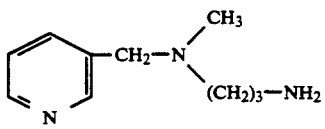

Employing the procedure of Example II, and 3-[N-(2-cyanoethyl)-N-methylaminomethyl]pyridine as the starting material, 9.87 g (87.7%) of the title product is obtained as a clear colorless oil after distillation at an oven temperature of 120° C. (0.01 torr).

$^1$H NMR (CDCl$_3$) δ1.37 (br s, 2H), 1.65 (q, 2H, J=7.0 Hz), 2.22 (s, 3H), 2.45 (t, 2H, J=7.0 Hz), 2.75 (t, 2H, J=7.0 Hz), 3.49 (s, 2H), 7.24 (dd, 1H, J=8.0, 5.0 Hz), 7.66 (dt, 1H, J=8.0, 2.0 Hz), 8.49–8.52 (m, 2H).

Anal. Calc. for $C_{10}H_{17}N_3$: C, 66.99; H, 9.57; N, 23.44. Found: C, 66.94; H, 9.47; N, 23.31.

EXAMPLE XXV

3/N-Methyl-N-[3-(N,N-dimethylamino)propyl]-aminomethyl/pyridine

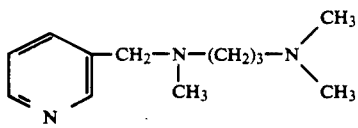

Employing the procedure of Example III, 4.75 g of 3-[N-3-aminopropyl)-N-methylaminomethyl]pyridine is methylated to provide 4.6 g (83.7%) of the title product as a clear colorless oil after distillation at an oven temperature of 115° C. (0.01 torr).

$^1$H NMR (CDCl$_3$) δ1.30–1.86 (m, 2H), 2.18 (s, 3H), 2.22 (s, 6H), 2.23–2.55 (m, 4H), 3.50 (s, 2H), 7.28 (dd, 1H, J=8.0, 5.0 Hz), 7.71 (dt, 1H, J=8.0, 2.0 Hz), 8.50–8.61 (m, 2H).

Anal. (tripicrate, mp 208°–10° C.) Calc. for $C_{30}H_{30}N_{12}O_{21}$ C, 40.28; H, 3,38; N, 18.79. Found: C, 40.50; H, 3.60; N, 18.99.

EXAMPLE XXVI (R,S)-1-(3-Aminopropyl)-2-(3-pyridyl)-1-azacycloheptane

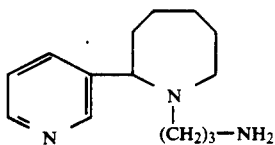

A solution of 500 mg (2.84 mmoles) of (R,S)-2-(3-pyridyl)azacycloheptane [Tetrahedron Lett., 1901 (1978)] in 1.15 ml of 2.4M of aqueous sodium hydroxide is treated with 395 mg (7.44 mmoles) of acrylonitrile and stirred at room temperature for 18 hours. A crude product is recovered, and bulb-to-bulb distillation at an oven temperature of 155° C. (0.02 torr) provides 635 mg of (R,S)-1-(2-cyanoethyl)-2-(cyanoethyl)-2-(3 -pyridyl-)azacycloheptane as a colorless oil.

A 625 mg sample of this product is reacted in accordance with the general procedure of Example II. The resultant material is chromatographed, and 435 mg (68.4%) of the title product is obtained as a colorless oil after distillation at an oven temperature of 135° C. (0.02 torr). $^1$H NMR (CDCl$_3$) δ1.42–1.98 (m, 10H), 2.12 (br s, 2H), 2.38–2.48 (m, 2H), 2.57 (q, 2H, J=3.5 Hz), 2.82 (dd, 1H, J=14.7, 8.2 Hz), 2.98 (dd, 1H, J=14.7, 8.2 Hz), 3.68 (ddd, 1H, J=7.2, 5.0, 1.4 Hz), 7.22 (dd, 1H, J=7.8, 4.8 Hz), 7.71 (dt, 1H, J=7.8, 2.1 Hz), 8.44 (dd, 1H, J=4.8, 1.4 Hz), 8.56 (d, 1H, J=2.1 Hz).

Anal. (tripicrate, mp 220°–1° C.) Calc. for $C_{32}H_{32}N_{12}O_{21}$: C, 41.74; H, 3.50; N.18.26. Found: C, 41.83; H, 3.58; N, 18.11.

EXAMPLE XXVII (R,S)-1-(N,N-Diethyl-3-aminopropyl-2-(3-pyridyl)pyrrolidine

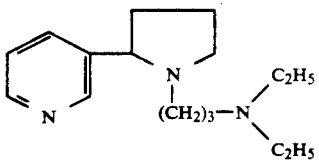

A solution of 2.0 g (9.74 mmoles) of (R,S)-1-(3-aminopropyl)-2-(3-pyridyl)pyrrolidine in 60 ml of acetonitrile is treated with a trace of bromocresol green indicator and sufficient 2N HCl in acetonitrile to produce a yellow color. The reaction mixture is stirred and cooled at 0° C. and treated with 2.0 g (45.4 mmoles) of freshly distilled acetaldehyde and 2.0 g (31.8 mmoles) of sodium cyanoborohydride. After being allowed to stir for 30 minutes at 0° C. and then at room temperature, additional 2N HCl in acetonitrile is added as needed to maintain a yellow color. After 2 days the reaction mixture is concentrated on a rotary evaporator.

The residue is treated with conc. HCl and heated on a water bath until gas evolution ceases. The acidified solution then is washed with ether, basified (50% KOH) and extracted into ether. Concentrations of the ether solution provides a crude product. The product is chromatographed, followed by bulb-to-bulb distillation at an oven temperature of 130° C. (0.01 torr) to yield 1.04 (40.8%) of the title product as a clear colorless oil.

$^1$H NMR (CDCl$_3$) δ0.98 (t, 6H, J=8 Hz), 1.35–2.68 (m, 11H), 2.73 (q, 4H, J=8.0 Hz), 3.18–3.50 (m, 2H), 7.30 (dd, 1H, J=8.0, 4.8 Hz), 7.75 (dt, 1H, J=8.0, 2.0 Hz), 8.55 (dd, 1H, J=4.8, 2.0 Hz), 8.58 (br d, 1H, J=2.0 Hz).

Anal. Calc. for $C_{16}H_{27}N_3$: C, 73.51; H, 10.41; N, 16.08. Found: C, 73.39; H, 10.19; N, 16.19.

EXAMPLE XXVIII (R,S)-6-(N,N-Dimethyl-3-aminopropyl)nicotine

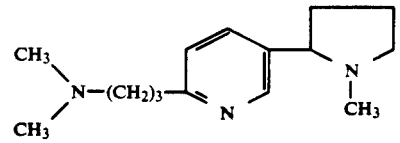

A solution of 1.37 g (13.56 mmoles) of diisopropylamine in 25 ml of tetrahydrofuran is stirred and cooled to −70° C., and treated with 7.80 ml (12.5 mmoles) of 1.6M n-butyllithium. A solution of 940 mg (5.34 mmoles) of (R,S)-6-methylnicotine [J. Org. Chem. 46, 3046 (1981)] in 5 ml of tetrahydrofuran was added to the cooled solution, and stirring is continued for 20 minutes. A 840 mg (5.83 mmoles) charge of granular chloroethyl dimethylamine hydrochloride is added. The solution is stirred for 30 minutes at −70° C., and then warmed to room temperature and stirred for 18 hours.

The reaction mixture is acidified with 6N HCl, washed with ether, basified (50% KOH) and extracted with ether. The ethereal solution is dried, concentrated, and distilled bulb-to-bulb at an oven temperature of 130° C. (0.05 torr) to provide a mixture of starting material and product. Purification is accomplished with a Harrison Chromatotron ® using a 4 mm silica gel plate and elution with chloroform, ethanol and ammonium hydroxide (85:14:1.5) solvent system. Bulb-to-bulb distillation of the combined and concentrated fractions at an oven temperature of 130° C. (0.05 torr) yields 458 mg (34.7%) of the title product as a clear colorless oil.

$^1$H NMR (CD$_2$Cl$_2$) δ1.57-2.38 (m, 8H), 2.04 (s, 3H), 2.12 (s, 6H), 2.55-2.78 (m, 2H), 2.86-3.25 (m, 2H), 2.33 (br d, 1H, J=8.0 Hz), 7.56 (dd, 1H, J=8.0, 2.0 Hz), 8.38 (br d, 1H, J=2.0 Hz).

Anal. (tripicrate) Calc. for C$_{33}$H$_{34}$N$_{12}$O$_{21}$: C,42.40; H,3.66; N,17.98. Found: C,42.37; H,3.76; N,17.86.

EXAMPLE XXIX

This Example illustrates pharmacological properties of nicotine analogs of the present invention.

The tranquilizing effects of invention nicotine compounds in rats are measured after intraperitoneal (IP) and intraventricular (IVC) administration in the form of hydrochloride salts.

"Sedation" is determined by measuring locomotion in an open field maze, and the response to noxious (air blast) stimuli. "Body tone" is estimated by handling rats and by the ability to hang from a rotating rod.

"Tranquilization" after intraventricular (IVC) injection is estimated from muscle weakness in all four limbs, body tone, and general activity.

Rating scale is 0−+++++. For comparative purposes, a dose of 5 mg/kg valium (IP) is ++++ in sedation and body tone, while 10 ug IVC is ++++ in tranquilization. The duration of action of the test compounds is 10–20 minutes IVC and about 30 minutes after IP injection.

The test results are summarized in the Table.

TABLE

| Nicotine Analog | Dose (IP) mg/kg | Sedation | Body Tone | Tranquilization (IVC) 50 ug |
|---|---|---|---|---|
| 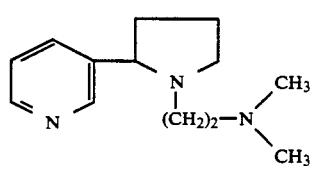 | 10<br>20 | +<br>++ | +<br>++ | ++++ |
| 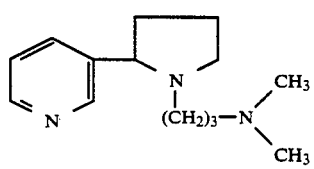 | 5<br>10<br>20 | +<br>++<br>+++ | +<br>+<br>++ | ++++ |
| 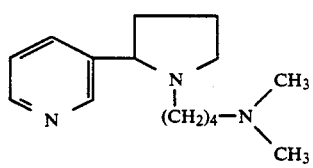 | 10<br>20 | +<br>+ | +<br>+ | +++ |
| 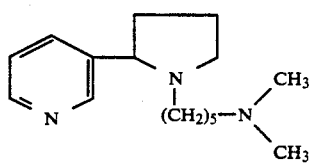 | 40 | ++ | ++ | +++ |
| 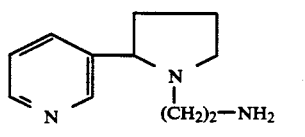 | | | | |
| 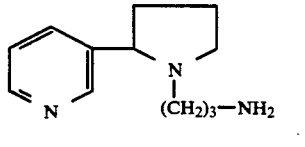 | 10<br>20 | 0<br>+ | 0<br>0 | +++ |
| 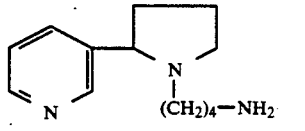 | 10<br>20 | 0<br>+ | 0<br>0 | +++ |

TABLE-continued

| Nicotine Analog | Dose (IP) mg/kg | Sedation | Body Tone | Tranquilization (IVC) 50 ug |
|---|---|---|---|---|
| 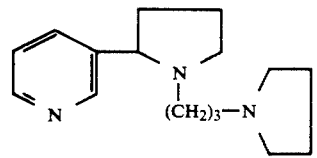 | 10<br>20 | +<br>++ | 0<br>++ | +++ |
| 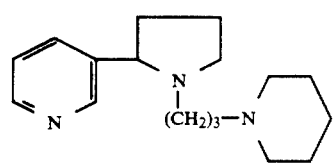 | 10<br>20 | 0<br>++ | 0<br>+ | ++ |
| 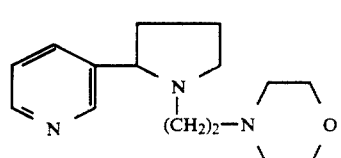 | 10<br>20 | 0<br>+ | 0<br>+ | + |
| 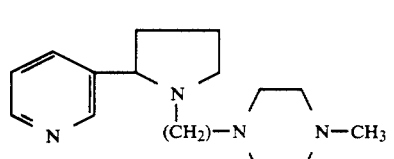 | 20<br>40 | ++<br>+++ | +<br>++ | ++++ |

What is claimed is:

1. A 3-pyridine derivative corresponding to the formula:

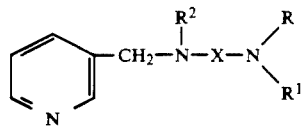

where R and R[1] are substituents selected from hydrogen and $C_1$–$C_4$ alkyl groups R[2] is a $C_1$–$C_4$ alkyl group; and X is a divalent acyclic $C_2$–$C_{10}$ hydrocarbyl radical.

2. A 3-pyridine derivative in accordance with claim 1 in the form of a pharmaceutically acceptable salt.

3. 3-[N-Methyl-N-(3-aminopropyl)aminomethyl]-pyridine.

4. 3-[N-Methyl-N-[3-(N,N-dimethylamino)propyl]-aminomethyl]pyridine.